United States Patent [19]
Sahouani et al.

[11] Patent Number: 6,051,290
[45] Date of Patent: Apr. 18, 2000

[54] ANISOTROPIC RETARDATION LAYERS FOR DISPLAY DEVICES

[75] Inventors: Hassan Sahouani, Hastings; Kim Marie Vogel, Lake Elmo, both of Minn.

[73] Assignee: 3M Innovative Properties Company

[21] Appl. No.: 09/311,087

[22] Filed: May 13, 1999

Related U.S. Application Data

[62] Division of application No. 08/924,189, Sep. 5, 1997.

[51] Int. Cl.[7] .............................. C09K 19/52; G02F 1/13; C07D 251/54
[52] U.S. Cl. ........................... 428/1.1; 428/1.5; 428/1.31; 428/426; 252/299.01; 252/299.5; 349/117; 349/181; 544/198; 544/211
[58] Field of Search ........................... 252/299.5, 299.01; 428/1.1, 1.5, 1.31, 426; 349/117, 181; 544/198, 211; 427/163.1

[56] References Cited

U.S. PATENT DOCUMENTS

| | | | |
|---|---|---|---|
| 2,400,877 | 5/1946 | Dreyer | 88/65 |
| 3,891,705 | 6/1975 | Diamond et al. | 544/198 |
| 4,030,812 | 6/1977 | Strebel | 350/157 |
| 4,031,092 | 6/1977 | Strebel | 428/426 |
| 5,124,824 | 6/1992 | Kozaki et al. | 359/73 |
| 5,132,147 | 7/1992 | Takiguchi et al. | 428/1 |
| 5,380,459 | 1/1995 | Kanemoto et al. | 252/299.01 |
| 5,406,396 | 4/1995 | Akatsuka et al. | 359/73 |
| 5,474,731 | 12/1995 | Morikawa et al. | 264/230 |
| 5,526,150 | 6/1996 | Mazaki et al. | 349/117 |
| 5,568,290 | 10/1996 | Nakamua | 359/63 |
| 5,631,051 | 5/1997 | Ito | 428/1.2 |
| 5,948,487 | 9/1999 | Sahouani et al. | 428/1 |

OTHER PUBLICATIONS

Goldmann, Daniela et al., "New disc–shaped triarylamino–1,3,5–triazines with heteroaromatic central cores", Liquid Crystals, vol. 21, No. 5, pp. 619–623 (1996).

Primary Examiner—Shean C. Wu
Attorney, Agent, or Firm—Robert J. Pechman

[57] ABSTRACT

A composition which includes the following compounds:

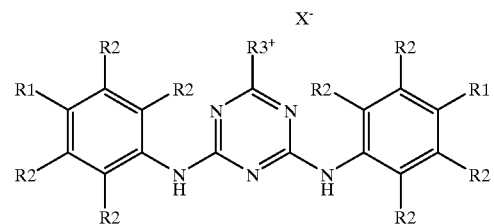

or

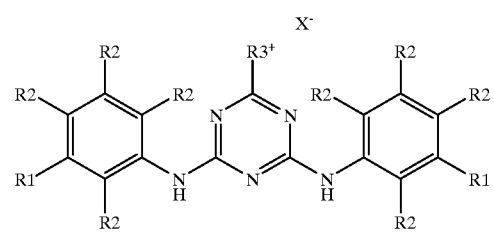

wherein $R^1$, which may be the same or different, is a hydrophilic group;

$R^2$, which may the same or different, is selected from the group consisting of electron donating groups, electron withdrawing groups, and electron neutral groups;

$R^3$ is a substituted or unsubstituted, positively charged heteroaromatic ring linked to the triazine backbone through a nitrogen atom in the $R^3$ ring; and $X^-$ is a counterion.

If $R^3$ is an unsubstituted pyridine, the counterion $X^-$ may be selected from any counterion other than $Cl^-$ and $OH^-$. Otherwise, the counterion $X^-$ may be selected from any counterion.

The compound may be applied to a substrate to form a birefingent optical retardation device. The retardation device may be used in display devices such as computers and the like to correct the phase and polarization states of the display's emitted light and improve image quality at viewing angles away from the normal.

16 Claims, 3 Drawing Sheets

ANISOTROPIC RETARDATION LAYERS FOR DISPLAY DEVICES

This is a divisional of application Ser. No. 08/924,189 filed Sep. 5, 1997.

BACKGROUND OF THE INVENTION

1. Field of the Invention

The present invention relates to an anisotropic composition of matter comprising a nematic triazine derivative with the structure below:

In the formulae I above, $R^3$ represents a positively charged, substituted or unsubstituted heteroaromatic ring linked to the triazine backbone through a nitrogen atom within the ring of $R^3$. If $R^3$ is an unsubstituted pyridine, the counterion $X^-$ may be any counterion except $Cl^-$ and $OH^-$. Otherwise, the counterion $X^-$ may be selected from any counterion. When at least one layer of the composition of matter is coated on a supporting substrate and dried, an optical retardation layer is produced which may be used to improve image quality in a display device. The properties of the composition and the substrate may be selected to form a birefringent retardation component that corrects the phase and polarization states of the display's emitted light to improve image quality at viewing angles away from the normal.

2. Description of Related Art

Low power consumption, light weight, and space saving capabilities make liquid crystal displays useful in many fields of application, such as in computers, avionics, and the like. The use of LCDs in some fields has been limited because the image shown on the display degrades as the viewer moves from a direct front view, normal to the display, referred to as a zero viewing angle, to a side view, or off-normal view, at a nonzero viewing angle. The viewing performance deteriorates as the observer moves away from the normal to the non-zero viewing angles in part because the light guiding property of the cell is compromised by the inherent birefringence of the liquid crystal layer and the slightly elliptical polarization state of light transmitted to the viewer. The birefringence of the liquid crystal layer tends to be more pronounced in super twisted nematic (STN) displays than in twisted nematic (TN) displays.

A number of techniques and materials have been developed to improve display quality for light at both normal incidence and at angles of incidence away from the normal.

In many currently available LCD devices, phase difference layers, typically multi-layered polymeric films, are placed in the path of the light transmitted to the viewer. These layers, referred to in the art as retardation or retardation layers, rely on optical anisotropy to modify the optical properties of the light emitted from the display. An optically anisotropic film exhibits differing refractive indices $n_x$, $n_y$, and $n_z$ for light polarized in planes parallel to the x, y, and z axes, respectively, wherein the x and y axes are in the plane of the retardation layer, and the z axis is normal to the plane of the layer, with the positive direction pointing away from the layer.

Optically anisotropic layers having refractive indices ($n_x$, $n_y$, $n_z$) for light polarized in planes parallel to the x, y, and z axes, respectively, are classified in various ways. If only one of the refractive indices of the layer, for example $n_x$, differs from the other two, $n_y$, and $n_z$, and the other two refractive indices ($n_y$, and $n_z$) are substantially equal, the material is said to be uniaxially birefringent. Moreover, if the unequal refractive index ($n_x$) is less than the two substantially equal refractive indices ($n_y$ and $n_z$), the material is negatively birefringent, while if the unequal refractive index ($n_x$) is greater than the two substantially equal refractive indices ($n_y$ and $n_z$), the material is positively birefringent.

If the material is in the form of a planar sheet, or plate, and if the optical axis is in the plane of the plate, the plate is referred to as an "A" plate. If the optical axis is perpendicular to the plane of the plate, the material is a "C" plate. If the optical axis is at some intermediate, or oblique, angle to the plane of the plate, the plate is an "O" plate. If the plate is an "A" plate and is negatively birefringent, the plate is an "A negative" plate.

Anisotropic films having particular relationships between $n_x$, $n_y$, and $n_z$ have been produced by a variety of means. For example, U.S. Pat. No. 5,124,824 discloses a retardation-plate comprising a liquid crystal material contained between two solid substrates, forming a structure similar to the liquid crystal device itself. The layer in U.S. Pat. No. 5,526,150 is produced by casting a liquid crystal polymer onto a glass plate and heat treating. The retardation plates described in the '824 and '150 patents are expensive, thick, and heavy.

U.S. Pat. No. 5,380,459 teaches that the refractive indices of polymeric films may be adjusted by stretching the film, aligning side chains with electrical or magnetic fields, or by applying shear stresses to the film surfaces. Phase retardation films produced by holding a stretched polymeric film between belts or rollers to constrain the surface while heating the film are disclosed in U.S. Pat. No. 5,474,731. Oriented liquid crystalline polymer films produced by coating a liquid crystalline polymer onto a stretched polymer film and heat treating to allow self-orientation are disclosed in U.S. Pat. No. 5,132,147. Production of compensating layers by heat treating and stretching of films requires a great deal of time, equipment, and cost, which is a disadvantage in a competitive manufacturing environment. In addition, when no single film or film and coating combination produce the desired values of $n_x$, $n_y$, and $n_z$, lamination of multiple films to achieve the desired overall refractive indices can become a burdensome task. If heat treating of layers is used to produce desired optical properties, other polymeric layers which may be present may be adversely affected by the heat treatment.

While the specific values of the refractive indices $n_x$, $n_y$, and $n_z$ necessary to produce a suitable retardation layer for a LCD depend upon the chemical structure of the materials in the display, as well as the process by which the materials are deposited, several useful relationships between $n_x$, $n_y$, and $n_z$ are known in the art. For example, U.S. Pat. No. 5,124,824 describes a polystyrene retardation layer in which the benzene rings of the polystyrene are oriented in the direction of the thickness of the film to provide a layer in which $n_z$ is greater than $n_x$ or $n_y$. Similarly, U.S. Pat. No. 5,380,459 describes polymeric materials having side groups containing aromatic groups or other groups containing multiple bonds. These polymeric materials have an $n_z$ greater than at least one of $n_x$ or $n_y$, and are stated to improve the off-axis viewing angle of a LCD. U.S. Pat. No. 5,406,396 describes a two-layer compensating film. The first layer has refractive indices satisfying the relationship $n_z > n_x = n_y$, while the second has a refractive indices such that, when the two layers are combined, results in an overall relationship of $n_x \geq n_z > n_y$ for the two-layer film. The compensating layer described in U.S. Pat. No. 5,526,150 has, in one example, refractive indices $n_x = 1.55$, $n_y = 1.55$, and $n_z = 1.75$, which are stated to significantly increase the viewing angle of a liquid crystal display in one direction. The disk-shaped liquid crystal layer described in U.S. Pat. No. 5,568,290 may be deposited on an anisotropic film to produces a material with an $n_z$ less than either $n_x$ or $n_y$.

U.S. Pat. No. 2,400,877 describes certain dyestuffs that form, under proper conditions, a linear or thread-like molecular structure. The '877 patent teaches that this structure, referred to in the art as a nematic phase or structure, may be preserved by careful evaporation and diffusion of a solution. The '877 patent further suggests that colorless or weakly colored nematic materials may be used in retarders or fractional wave plates to increase the contrast of displays such as cathode ray tubes (CRTs) and LCDs. However, the materials described in the '877 patent become soap-like, or smectic, before drying, and are not useful in LCD applications.

U.S. Pat. No. 4,031,092 to Strebel describes a class of triazine derivatives that form a nematic phase in dilute aqueous solution. The compounds described in the '092 patent, generally referred to as 1-[4,6 di(carboxyanilino)-1,3,5-triazine-2-yl] pyridinium salts, form birefringent, varnish-like films when dried. If applied at a thickness of about 0.1 to 5 microns onto a glass substrate which has been surface oriented by unidirectional rubbing, the films may be used to produce a retardation plate. Films of about 0.40 to about 0.65 microns thickness are stated to provide retardations of about 65° to about 120°.

The '092 patent states the birefringent films formed from the 1-[4,6 di(carboxyanilino)-1,3,5 triazine-2-yl] pyridinium salts are "by normal illumination . . . unnoticeable and substantially colorless." The Stebel patent further states that "slight residual color of the film may usually be discharged when the film is heated above about 150–200° C. without greatly changing the birefringence or anisotropy." However, the ammonium hydroxide solutions described in the '092 patent are too dilute to provide sufficiently thick films for LCD applications. When coated at a thickness of greater than 1 μm as required for display applications, the present inventors have discovered that the compounds described in the '092 patent have a yellowish tint which distorts the blue colors in the display and causes the display colors to appear purple. In addition, ammonium chloride crystals form when the ammonium hydroxide solutions of the pyridinium salts described in the '092 patent are coated and dried on a substrate, which causes significant problems in display applications. The aqueous solutions described in the '092 patent are also quite unstable, and their limited shelf life is not acceptable for commercial applications. The solutions described in the '092 patent may be applied to glass substrates only, and will not wet plastic substrates, which represents a serious limitation. The Strebel patent further requires that the substrate be oriented by a rubbing step which is sometimes difficult to perform consistently in a manufacturing setting and which can limit the types of substrates onto which the material can be coated.

There is therefore a need to produce durable, optically anisotropic layers for a wide variety of display applications that can be adapted to enhance the off-axis viewing performance. The materials described in the '092 patent have certain advantages, but compounds are required which are colorless, more easily manufactured and stored, and may be applied directly to a variety of polymeric substrates without the need for extraordinary processing steps. The present invention has been completed based on these needs

SUMMARY OF THE INVENTION

The present invention is an optically anisotropic layer which may be applied on an isotropic or anisotropic supporting substrate to provide a birefringent optical retardationdevice.

The anisotropic layer of the present invention comprises an aqueous composition of matter comprising a compound with the general structure below:

In these formulae I, the $R^1$s, which may be the same or different, are hydrophilic groups. The $R^2$s can be independently chosen to be hydrogen, an electron donating group, an electron withdrawing group or an electron neutral group. $R^3$ is a positively charged, substituted or unsubstituted heteroaromatic ring linked to the triazine backbone through a nitrogen atom within the ring of $R^3$. The substituent for $R^3$ may be selected to determine the properties of the anisotropic layer, for example, the desired color of the layer. If $R^3$ is an unsubstituted pyridine, $X^-$ is a counterion that may be selected from any counterion except $Cl^-$ and $OH^-$. Otherwise, the counterion $X^-$ may be selected from any counterion. Compounds with the above structure are soluble in basic aqueous solutions having a suitably adjusted pH.

Compounds suitable for the anisotropic layer of the present invention form highly ordered structures when coated as an aqueous solution and dried on a substrate. The materials in the layers of the present invention have very high optical anisotropies, and may be coated in very thin layers, thereby minimizing thickness contributions to undesirable optical properties in display devices. The anisotropic layer of the present invention has a refractive index in the thickness, or z, direction of the layer that is slightly less than or substantially equal to one of the refractive indices $n_x$ and $n_y$ in the plane of the layer The present invention further includes a birefringent optical retardationcomponent which comprises at least one layer of the anisotropic material on a suitable substrate. The properties of the anisotropic material and the supporting substrate may be selected to provide optical retardationcomponents with widely varying effects on display properties such as color, off-normal viewing performance and the like. The substrate may be flexible or inflexible, and may comprise a wide variety of materials, including, for example, glass and polymeric compounds.

In addition, the present invention extends to an electronic device that includes a birefringent optical retardationcomponent with at least layer of the anisotropic material.

Very thin layers of the invention provide good color and enhanced viewing angle performance to TN and STN displays.

DETAILED DESCRIPTION OF THE INVENTION

A common liquid crystal display, or LCD, is made up of a two dimensional array of picture elements, or pixels. A pixel 2 is shown in exploded view in FIG. 1. The pixel 2 may include several optical elements through which a light 20 passes before reaching a viewer 70.

Figure 1:
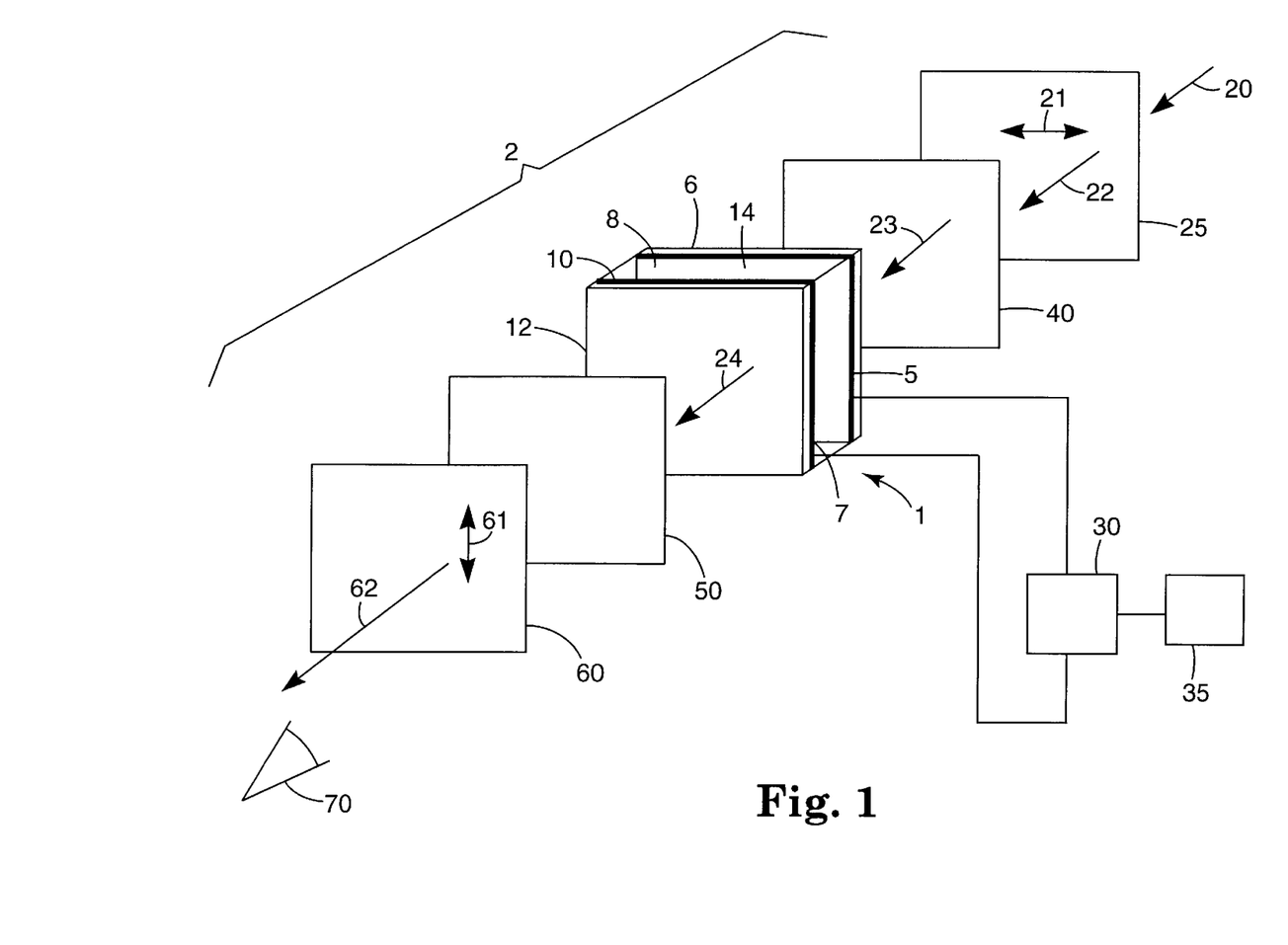
FIG. 1 is an exploded view of one pixel of an embodiment of a display device that includes a retardation plate with the layered material of the present invention.

A first polarizer 25 transmits, as light 22, that portion of the light 20 which is polarized in the direction indicated by an arrow 21. The polarized light 22 passes through a compensating plate 40. The compensating plate 40 adjusts the polarization and other optical properties of the light 22 to compensate for undesired polarization and phase properties which may be introduced by a liquid crystal device element 1. A transmitted light 23 emerges from the compensating plate 40 and enters the liquid crystal device element 1.

The liquid crystal device element 1 is made up of a liquid crystal material 14, contained between a pair of transparent plates 6 and 12. The plates 6 and 12 are typically made of glass, but may also be made of a polymeric material. Interposed between the liquid crystal material 14 and the plates 6 and 12, adjacent to plates 6 and 12, are electrodes 5 and 7. The electrodes 5 and 7 are electrically connected to a driver 30, which receives an image signal from a signal source 35. Interposed between the electrodes 5 and 7 and the liquid crystal material 14 are alignment layers having alignment surfaces 8 and 10.

The alignment surfaces 8 and 10 typically comprise a polymeric film that is surface treated to align, in a preferred direction, the molecules of liquid crystal material 14. Typical treatments for the alignment surfaces 8 and 10 include rubbing the surface with a slightly abrasive material such as paper or cloth in a single direction. The resulting molecular alignment of the liquid crystal molecules at the alignment surfaces 8 and 10 generally parallel to these surfaces and oriented along the direction of rubbing. When the alignment directions at the alignment surfaces 8 and 10 differ from one another, and when no electrical signal is applied to the electrodes 5 and 7, the liquid crystal molecules in layer 14 change their alignment from that of surface 8 to that of surface 10 in an orderly fashion to produce an optical activity in layer 14. As a result of this optical activity, the light 23, which is linearly polarized in the direction 21, will have its plane of polarization rotated through an angle, called the twist angle, which depends on the angular difference in liquid crystal molecular alignment directions at the alignment surfaces 8 and 10. If the twist angle is in the range of about 90°, and liquid crystal material 14 is a nematic liquid crystal material, the liquid crystal device is said to be a twisted nematic, or TN, device. If the twist angle is significantly greater than 90°, in the range of 200°–300°, for example, the device is called a supertwisted nematic, or STN, device.

If a sufficiently strong electrical field, normally only a few volts between the electrodes 5 and 7, is applied through the liquid crystal material 14, the molecular alignment of the material 14 previously produced by the alignment surfaces 8 and 10 is overcome, and the liquid crystal material assumes a homeotropic state. The term homeotropic means that the liquid crystal molecules are aligned in a generally parallel orientation normal to the plane of the electrodes 5 and 7, rather than in the surface aligned twisted orientation produced by the effects of alignment layers 8 and 10. This makes the liquid crystal material 14 optically inactive, so that the direction of the plane of polarization of the light 23 is unaltered by the device element 1. Thus, the light 24 emerging from device element 1 may be plane polarized in either a direction parallel to the polarizer direction 21 or in a plane rotated from this direction by an amount equal to the twist angle of device element 1 device element 1. The direction of plane polarization depends on whether the driver 30 applies an electrical signal between the electrodes 5 and 7.

A retardation plate 50 may optionally be present to further adjust or correct the optical state of the light 24 emerging from the device element 1. For example, if the light 24 emerges from the device element 1 in an elliptically polarized state, rather than in a linearly polarized state, plate 50 can be made suitably birefringent to correct the polarization of light 24 to a linear state.

An analyzer 60 is a polarizer that passes light polarized in a plane parallel to a direction indicated by an arrow 61, while blocking light polarized in the orthogonal direction. The analyzer 60 blocks or passes light emerging from the device element 1, depending on whether an electrical signal is applied to the electrodes 5 and 7. Thus, when the viewer 70 views the device element 1 through the analyzer 60, it will appear to be either illuminated or dark, depending on whether the driver 30 applies a signal to the device element 1. Therefore, since the device element 1 is but one element of the overall display device, an entire image can be created by the complete array of pixels, each one being made optically active or inactive by the application of an electrical field from a driver such as driver 30. While retardation plates 40 and 50 are shown adjacent to first polarizer 25 and second polarizer 50, respectively, their location is not restricted to these two positions. Plates 40 and 50 can be effective if placed anywhere between polarizer 25 and polarizer 50. Similarly, while two retardation plates are shown, there is no particular limitation on the number of plates used. In some cases one retardation plate may be sufficient, and in other cases three or more plates may be needed.

The present invention is an optically anisotropic layer which, when applied in at least one layer on a supporting substrate, forms a birefringent compensating component for use in a display. The location of the birefringent component in the display may vary widely depending on the properties of the substrate selected, the type of display, and the required viewing parameters.

As used herein, optical anisotropy will be taken to mean that at least one of the refractive indices $n_x$, $n_y$, and $n_z$, for light linearly polarized in planes parallel to the x, y, and z directions, respectively, is unequal to one or both of the other refractive indices. It will be assumed, for purposes of description, that the anisotropic layer of the present invention is planar, in the x-y plane, with the positive z axis being normal to the x-y plane and pointing away from the supporting substrate. It will be readily apparent to one skilled in the art, however, that other, nonplanar, versions of the present invention could be produced.

The compounds from which the anisotropic layers of the present invention are made are triazine derivatives with a substituted or unsubstituted positively charged nitrogen-containing heteroaromatic ring. While not wishing to be bound by any theory, the present inventors believe that the aromatic, positively charged ring interacts with other hydrophilic substitutents on the triazine backbone to provide a structure that readily aggregates and exhibits liquid crystalline properties.

The anisotropic layer of the present invention is compound with the formulae below:

In the formulae I above, $R^1$, which may be the same or different, is a hydrophilic group. For example, $R^1$ may be selected from carboxylic acid (COOH), sulfonic acid ($SO_3H$), sulfinic acid ($SO_2H$), sulfonamide ($SO_2NH_2$) or phosphate ($PO(OH)_2$) groups. $R^1$ is preferably a carboxylic acid group or a sulfonic acid group, and is most preferably a carboxylic acid group. The most preferred location for $R^1$ is para with respect to the amino linkage to the triazine backbone of the compound.

The $R^2$s in formulae I, which may the same or different, may be selected from any electron donating group, electron withdrawing group or electron neutral group. Preferably, $R^2$ is hydrogen or a substituted or unsubstituted alkyl group, and most preferably H.

In the formulae I, $R^3$ may be selected from substituted or unsubstituted, positively charged heteroaromatic rings linked to the triazine backbone through a nitrogen atom within the ring of $R^3$. $R^3$ can be, but is not limited to, beteroaromatic rings derived from pyridine, pyridazine, pyrimidine, pyrazine, imidazole, oxazole, thiazole, oxadiazole, thiadiazole, pyrazole, triazole, triazine, quinoline, and isoquinoline. Preferably $R^3$ is a pyridine ring.

A substituent for the heteroaromatic ring $R^3$ may be selected to determine the properties of the anisotropic layer, for example, the desired color for the layer. The substituent for $R^3$ may be selected from, but is not limited to, any of the following substituted or unsubstituted groups: alkyl, carboxyl, amino, alkoxy, thio, cyano, amide and ester. The substituent for $R^3$ is preferably a substituted amino or pyrrolidino group, more preferably an alkyl substituted amino group, and most preferably a dimethylamino group. Most preferably, the substitutent is located at the 4 position on a pyridine ring.

The counterion $X^-$ in formulae I may vary widely depending on the solvent selected and on the intended application. If $R^3$ is an unsubstituted pyridine, the counterion $X^-$ may be selected from any counterion except $Cl^-$ and $OH^-$. The preferred counterion $X^-$ is $HSO_4^-$, but other counterions are also possible including, but not limited to, $Cl^-$, $OH^-$, $CH_3COO^-$, $CF_3COO^-$, $BF_4^-$, $PF_6^-$, $SbF_6^-$, $CH_3SO_3^-$, $CF_3SO_3^-$, and $PhCO_2^-$.

Otherwise, the counterion $X^-$ in formulae I may be selected from any counterion. If $R^3$ is not an unsubstituted pyridine, the preferred counterion $X^-$ is again $HSO_4^-$, but other counterions are also possible including, but not limited to, $Cl^-$, $OH^-$, $CH_3COO^-$, $CF_3COO^-$, $BF_4^-$, $PF_6^-$, $SbF_6^-$, $CH_3SO_3^-$, $CF_3SO_3^-$, and $PhCO_2^-$.

The compounds of the invention may be prepared as aqueous solutions, or may be prepared as salts which can later be re-dissolved to form an aqueous solution. The compounds of the invention are typically soluble in basic aqueous solutions having a suitably adjusted pH. While $NH_4OH$ was found to be a suitable base for adjusting the pH to an appropriate level, the invention is not limited to this base, and other suitable bases such as, for example, cesium hydroxide, may also be used.

The optically anisotropic layers of the present invention can be formed by coating aqueous solutions containing the compounds of formulae I onto suitable substrates and drying. The drying temperature may vary widely depending on the materials selected and the required drying time, but typically a moderate temperature of about 70° C. to about 80° C. is preferred to avoid crystallization.

As required for a particular application, is it also possible to coat other layers on the anisotropic layer, such as, for example, optically neutral protective layers, other anisotropic layers, or adhesive layers.

Properties of the coated anisotropic layers may be enhanced, in some cases, by incorporating effective amounts of various additives to the coating solution. For example, addition of less than about 5% by weight, based on the total weight of coating solution, preferably about 0.1% to about 1% by weight, of a long chain alcohol, has been found, in some cases, to improve the optical performance of the coated layer. Examples of suitable alcohols include pentanol.

Nonionic surfactants such as, for example, the surfactant available from Rohm & Haas, Philadelphia, Pa., under the trade designation Triton X-100, have been found useful in some cases to improve coatability and adhesion of the coating to the substrate. Typically, less than about 5% by weight, preferably less than about 1% by weight, and most preferably about 0.1% by weight of the surfactant may be used.

Small amounts, typically less than about 0.1% by weight, preferably about 0.04% by weight, of a chiral compound such as, for example, (+)-2,3-di-p-tolyl-d-tartaric acid, brucine sulfate, tartaric acid and cholesterol, may enhance viewing angle performance of anisotropic layers used in STN displays. See, for example, Radley et al., *Cholesteric States of Micellar Solutions,* Molecular Physics, 1978, vol. 35, No. 5, pages 1405–1412.

Addition of less than about 5% by weight, more preferably about 1 to about 2% by weight, of water soluble polymers such as, for example, polyvinyl alcohol, polyvinyl pyrrolidone, and polyethylene glycols may enhance the chemical, mechanical, or other physical properties the coated layer, provided they are not added in such quantities as to inhibit the formation of the ordered structure of the coated layer.

Substrates to which solutions of the compounds of formulae I may be applied include glass, as well as transparent or substantially transparent polymeric films having suitable surface properties. These substrates may be flexible or rigid and may be made of anisotropic or isotropic materials to provide the desired level of optical retardation or color for a particular display application. For example, anisotropic substrates, such as polyimide, are useful in cases wherein the desired combination of $n_x$, $n_y$, and $n_z$ cannot be produced by the anisotropic coating layer alone. Suitable substrate materials include, but are not limited to, polymethyl methacrylate, polyethylene terephthalate, polyamide, polyimide, polycarbonate, polystyrene, styrene-acrylonitrile and acrylonitrile-methylacrylate.

The optically anisotropic layer of formulae I may also be coated on one or several different substrates made of symmetric type C, A, O or other birefringent materials. The birefringent substrate materials may either be coated or made from stretched, flexible, polymeric or non-polymeric films to provide a compensating plate for a particular application. Examples of these birefringent substrate materials include, but are not limited to, tricellulose acetate, polystyrene, polypropylene, polyethylene terepthalate, and copolymer films of the formula A-B or A-B-C such as styrene-acrylonitrile, methacrylonitrile, and styrene methacrylonitrile.

The substrates may be surface treated by, for example, corona treatment, or may contain a primer or other intermediate layer to aid in coatability or coating adhesion. It is typically not necessary to provide mechanical surface preparation such as rubbing or other alignment or orientation steps, but these steps may be useful to achieve some non-conventional orientation necessitated by some applications.

The method of coating is not particularly limited, though it is preferred that a shear stress be applied to the solution as it is applied to the substrate. The shear stress aligns the lyotropic, nematic structure in the monodomain structures of the compounds of the present invention with an optical axis in the direction of the coating. Coating techniques ranging from a wirewound coating rod to extrusion dies are all suitable for deposition of the material onto a substrate. Extrusion die methods, when accompanied by some shear, are generally preferred, and provide enhanced control of coating thickness.

When at least one layer of the compound of formulae I above is coated on a substrate and dried, a compensating plate is formed that may be used in a wide variety of optical devices to modify its optical performance. The compensating plates of the present invention may be used in a LCD device as illustrated by the plates 40 and 50 of FIG. 1, for example, and may also be used in other devices as a component of an anti-glare filter. The optically modified displays may be used in a wide variety of electronic devices, such as computers, calculators, watches, and the like.

The present invention will be further described with reference to the following non-limiting examples.

Phase retardation R of one polarization component of polarized light relative to an orthogonal polarization component can be measured by a variety of methods. In the following examples, retardation R of the retardation layer, defined as R=Δnd, wherein Δn=($n_x$–$n_y$) and $n_x$ and $n_y$ are refractive indices for light polarized parallel to the x and y axes respectively, and d is the thickness of the retardation layer, was measured photometrically, using the crossed polarizer method. In this method, the sample layer of anisotropic retardation material was placed between two polarizers oriented with their polarization directions at 90° to one another. An optical axis of the sample was oriented at 45° to the polarization direction of the first polarizer. A beam of monochromatic green light, filtered to have a wavelength centered at 550 nm, was passed through the combination of polarizers and sample, and the intensity I of the emerging light was measured photometrically. In this instance, the second polarizer, the polarizer through which the light passes after passing through the sample, acted as an analyzer for the polarized light. A baseline intensity reading $I_0$ was taken by orienting the polarizers in a polarizing direction parallel to one another and orienting the sample so as to also place one of its optical axes parallel to this direction. As explained in Wahlstrom, *Optical Crystallography,* John Wiley and Sons, New York, 1979, pp. 169–171, once I and $I_0$ have been determined, Retardation R can be calculated by the following equations:

$$\sin^2(\delta/2)=I/I_0,$$

wherein $\delta=2\pi\Delta nd/\lambda$, so that

$$R=\Delta nd=\delta\lambda/(2\pi)=(\lambda/\pi)\sin^{-1}(I/I_0)^{1/2},$$

wherein $\sin^{-1}$ ($I/I_0$) is in radians.

Measurements of R were carried out with the sample retardation layer oriented normal, that is to say zero incidence angle to the incident beam of light, and with the sample oriented at nonzero angles of incidence to the beam of light.

EXAMPLE 1

In formulae I, if $R^1$ is COOH, $R^2$ is hydrogen, $R^3$ is pyridinium, and $X^-$ is sulfate, the resulting compound is 1-[4,6-di(4-carboxyanilino)-1,3,5-triazin-2-yl]pyridinium hydrogen sulfate, which was prepared in the following manner, according to the reaction shown.

To a 500 ml three neck round-bottom flask with a thermometer, mechanical stirrer and condenser was added 117 ml of anhydrous pyridine. The mixture was heated to 70° C. and 39 g of 4,4'-[(6-chloro-1,3,5-triazine-2,4-diyl) diimino]bis-benzoic acid was added to give a heterogeneous mixture. The temperature was slowly increased to 85° C. and heated for one hour while the suspension was stirred vigorously. The mixture was cooled to 15° C. and the solid was collected by suction filtration, washed with pyridine, and air dried overnight at room temperature to give 47.69 g of a yellow solid.

A 4.44 g sample of the solid was dissolved in 115 ml of water containing 1.62 ml of 30% aqueous ammonium hydroxide solution. The mixture was stirred for ten minutes and filtered to remove a small amount of solid. The filtrate was transferred to a 250 ml three neck round bottom flask with a mechanical stirrer and a pH meter.

A solution of 4% by weight sulfuric acid in water was added slowly dropwise until the pH reached about 3.5. The solid was collected by suction filtration, stirred in 100 ml of water, and collected by filtration. The solid was then heated to 56° C. in 200 ml of acetone, collected, and air dried.

The resulting compound was subjected to nmr analysis, which showed a structure consistent with 1-[4,6-di(4-carboxyanilino)-1,3,5-triazin-2-yl]pyridinium hydrogen sulfate, which will hereinafter be called compound A.

EXAMPLE 2

A coating solution of compound A was prepared by dissolving 10 g of compound A in 100 g of a 0.5 to 2% aqueous solution of $NH_4OH$. To this solution was then added 0.2 ml of pentanol, 0.1 ml of a surfactant available from Rhom & Haas, Philadelphia, Pa. under the trade designation Triton X-100, and 0.04% by weight, based on the weight of compound A, of a chiral compound, brucine sulfate. This viscous solution was coated onto an isotropic polymethylmethacrylate film substrate to a coating thickness of 20 $\mu$m using a wire wound coating rod at a speed which provided a suitable shear during the coating. The dry coating thickness was about 1.2 $\mu$m.

The resulting phase retardation of this anisotropic layer was found to be $\Delta n \times d = 200$ nm, where d was the thickness of the dry layer. The phase retardation was measured directly by placing the sample between crossed polarizers and using the following formula:

$$I = I_0 \sin^2 (\delta/2),$$

where $\delta = (2\pi \Delta n d)/\lambda$;

$I_0$=the light transmission of the parallel polarizers with the sample between them in a neutral position; and I=the light transmitted with the sample between the polarizers at 45° to the transmission axis.

Compound A is bright yellow between crossed polarizers. When used as a phase compensating layer in position 50 in FIG. 1 for a liquid crystal display of the STN type, this anisotropic layer provided both color compensation, in that the display was black and white, rather than purple and yellow. In addition, the off-normal viewing angle of the display was enhanced.

Figure 2:
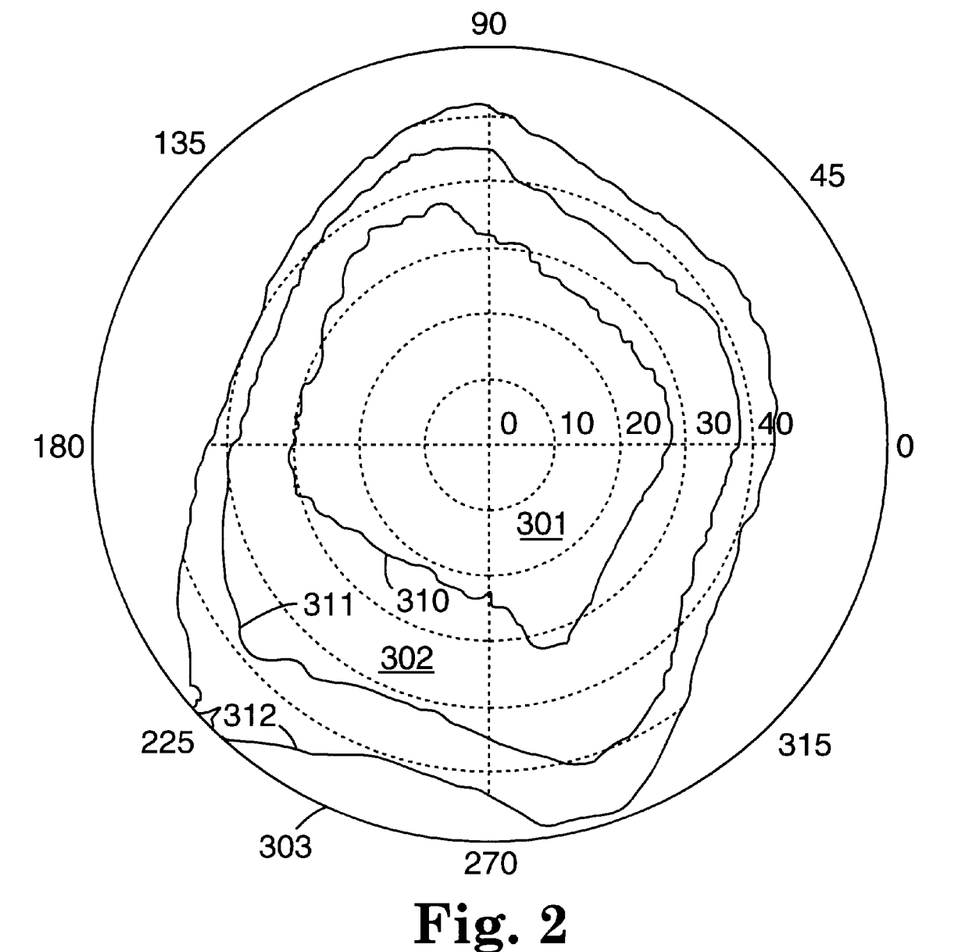
FIG. 2 is an isocontrast plot of an STN cell in which a film of the present invention, combined with a polyimide layer, is used as a retardation plate.
Figure 3:
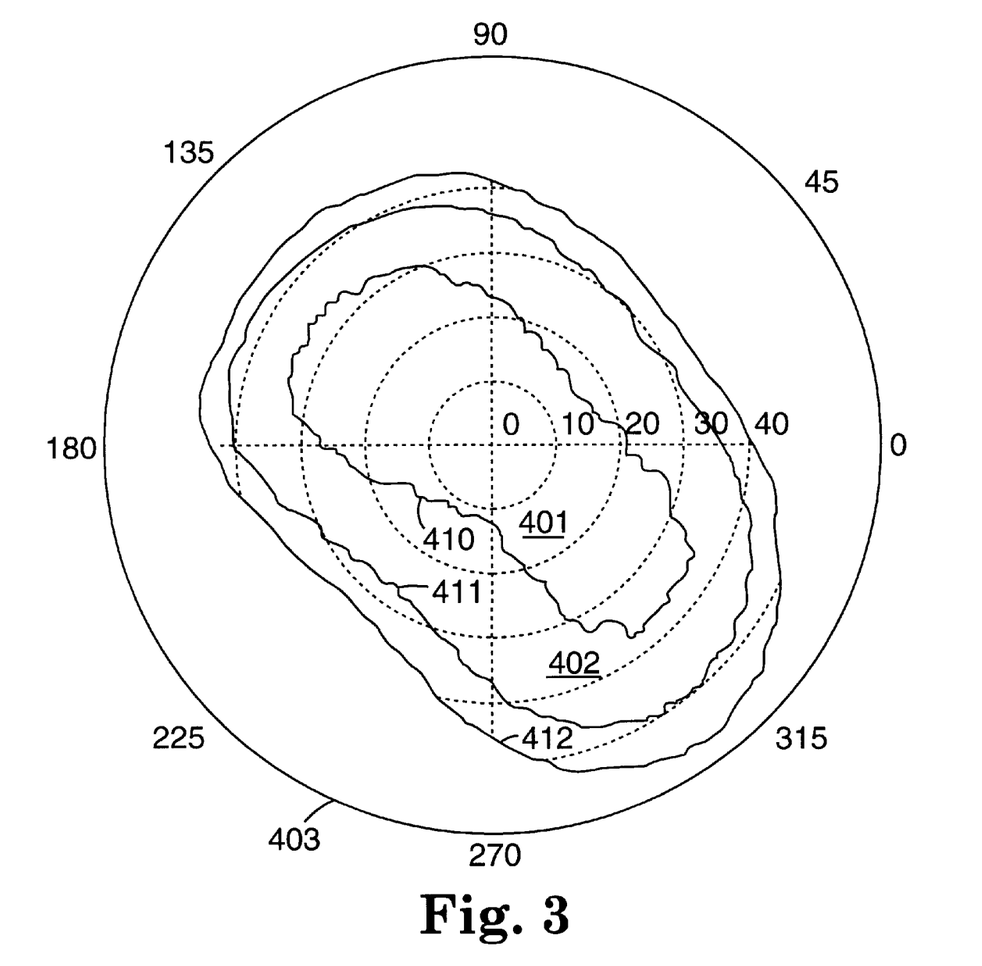
FIG. 3 is an isocontrast plot of an STN cell with two conventional polymeric retardationfilms.

FIG. 2 is a plot of isocontrast curves for the retardation layer of the present example. In FIG. 2, the dashed concentric circles define viewing angle $\phi$, in degrees, away from the normal to the display, while the angular position around the circular plot, measured in a counterclockwise direction, represents the azimuthal viewing position. Line 310 defines region 301, which is the region in which the contrast ratio between light and dark pixels is in the range of 11.99 to 18.00. In region 302, which falls between lines 310 and 312, the contrast ratio between light and dark pixels falls in the range of 6.00 to 11.99. Line 311 in region 302 defines the viewing positions at which the contrast is at the midpoint of the range between 6.00 and 11.99. At still larger viewing angles, in region 303, defined by lines 312 and 313, the contrast ratio drops to 6.00 or below. It should be noted that not only do regions 301 and 302 encompass viewing angles well over 30°, for virtually all azimuthal viewing positions, but that the isocontrast regions are quite symmetrical. This is helpful in avoiding sudden changes in viewability with change in viewing position. In comparison, FIG. 3 shows isocontrast plots for the same display without the retardation film of the present example. It will be noted that both region 401, which is the region in which the contrast ratio between light and dark pixels is in the range of 11.99 to 18.00, and region 402, which is the region in which the contrast ratio is in the range of 6.00 to 11.99, are narrow and elongated, which would lead to poor viewability for an observer viewing the display from an upper right position or from a lower left position.

EXAMPLE 3

A coating solution was prepared as in Example 2, except that only 5 g of compound A was dissolved in the 100 g of 0.5%–2.0% aqueous solution of $NH_4OH$. This made the wet coating thinner, to produce a dry layer of a lyotropic material with a thickness of less than 0.5 μm and only a slight yellow tint. When used as layer 50 in FIG. 1, this layer provided an increase in bottom viewing angle of about 10% in the TN display. The measurement procedure used was the same as in Example 2 above.

EXAMPLE 4

In formulae I, when $R^3$ is pyridinium, the substituent for $R^3$ is 4-dimethylamino, and $X^-$ is $HSO_4^-$; the resulting compound is 1-[4,6-di(4-carboxyanilino)-1,3,5-triazin-2-yl]-4-(dimethylamino)pyridinium hydrogen sulfate, which was prepared by the following reaction and procedure.

EXAMPLE 5

A coating solution was prepared by dissolving 10 g of compound B in 100 g of 2% aqueous solution of $NH_4OH$ containing about 0.1% by weight of total solution of the nonionic surfactant Triton X-100. This solution was coated onto a non-birefringent substrate using the same methods described in Example 2 to a dry coating thickness of 1–2 μm and was found to have a phase retardation of about 200 nm.

This very clear water white layer was then introduced into an STN stack. The layer produced in this example was colorless, not yellow like the layer produced in Example 2, and would be expected to be more desirable for display applications than the layer in Example 2. In addition, the enhancement of the viewing angle performance obtained in Example 2 as also obtained with this compound, and no chiral material or long chain alcohol was required.

EXAMPLE 6

A 1.2 μm thick layer of compound B, prepared as described in Example 5, with retardation of about 200 nm, To a 250 ml three necked round bottom flask with a condenser was added 7.0 g of 4,4'-[(6-chloro-1,3,5-triazine-2,4-diyl)diimino]bis-benzoic acid, 2.2169 g of 4-dimethylaminopyridine, and 63 ml of dimethyl sulfoxide. The mixture was heated to 90° C. for a total of 3 hours, filtered hot, washed with dimethylsulfoxide and acetone, and air dried to give 4.47 g of a white solid. A 3.3 g sample of the solid was dissolved in 86 ml of water containing 6 ml of 30% aqueous ammonium hydroxide. The mixture was stirred for 20 minutes to dissolve the solid and then filtered. The filtrate was acidified to a pH of 3.22 with 111 ml of a solution prepared by adding 2.4 ml of 18M sulfuric acid to 108.6 ml of water. The solid was collected by suction filtration, slurried in 100 ml of water, again collected, heated to 56° C. in 100 ml of acetone, and collected yet again. The solid was then heated to 56° C. in 100 ml of acetone, collected, and air dried to give 3.0 g of a product.

An nmr analysis showed the resulting product to have a chemical structure consistent with 1-[4,6-di(4-carboxyanilino)-1,3,5-triazin-2-yl]-4-(dimethylamino) pyridinium hydrogen sulfate, which will hereinafter be called compound B.

was applied to a negatively birefringent substrate layer of polyimide using the procedure of Example 2. The combination formed an A:C construction with an out-of plane retardation larger than about 100 nm.

The addition of the A:C plate increased the horizontal viewing angle of the STN display to about 120°. This represents a major improvement in the viewing angle of the STN display without any negative effects on the color performance of the display.

It will be understood that the exemplary embodiments described herein in no way limit the scope of the invention. Other modifications of the invention will be apparent to those skilled in the art in view of the foregoing description. These descriptions are intended to provide specific examples of embodiments which clearly disclose the present invention. Accordingly, the invention is not limited to the described embodiments or to the use of the specific elements, dimensions, materials or configurations contained therein. All alternative modifications and variations which fall within the spirit and scope of the appended claims are included in the present invention.

We claim:

1. An optical retardation plate comprising a layer of a composition on a substrate, wherein the layer comprises the following composition:

wherein

R$^1$, which may be the same or different, is a hydrophilic group selected from the group consisting of carboxylic, sulfonic, sulfonamide and phosphate groups;

R$^2$, which may be the same or different, is selected from the group consisting of alkyl groups and hydrogen;

R$^3$ is selected from the group consisting of:

(a) unsubstituted, positively charged heteroaromatic rings linked to the triazine backbone through a nitrogen atom in the R$^3$ ring, with the proviso that R$^3$ is not a pyridine ring, with X$^-$ as a counterion selected from the group consisting of Cl$^-$, OH$^-$, SO$_4$H$^-$, CH$_3$COO$^-$, and CF$_3$COO$^-$, BF$_4^-$, PF$_6^-$, SbF$_6^-$, CH$_3$SO$_3^-$, CF$_3$SO$_3^-$, and PhCO$_2^-$—;

(b) substituted, positively charged heteroaromatic rings linked to the triazine backbone through a nitrogen atom in the R$^3$ ring, wherein the substituents for R$^3$ are selected from the group consisting of alkyl, carboxyl, amino, alkoxy, thio, cyano, amide and ester groups, with X$^-$ as a counterion selected from the group consisting of Cl$^-$, OH$^-$, SO$_4$H$^-$, CH$_3$COO$^-$, and CF$_3$COO$^-$, BF$_4^-$, PF$_6^-$, SbF$_6^-$, CH$_3$SO$_3^-$, CF$_3$SO$_3^-$, and PhCO$_2^-$; and (c) unsubstituted, positively charged pyridine rings linked to the triazine backbone through the nitrogen atom in the R$^3$ ring, with X$^{31}$ as a counterion selected from the group consisting of SO$_4$H$^-$, CH$_3$COO$^-$, and CF$_3$COO$^-$, BF$_4^-$, PF$_6^-$, SbF$_6^-$, CH$_3$SO$_3^-$, CF$_3$SO$_3^-$, and PhCO$_2^-$.

2. A display comprising an optical retardation plate, wherein the retardation plate comprises a substrate with a layer thereon, the layer comprising the following composition:

wherein

R$^1$, which may be the same or different, is a hydrophilic group selected from the group consisting of carboxylic, sulfonic, sulfonamide and phosphate groups;

R$^2$, which may be the same or different, is selected from the group consisting of alkyl groups and hydrogen;

R$^3$ is selected from the group consisting of:

(a) unsubstituted, positively charged heteroaromatic rings linked to the triazine backbone through a nitrogen atom in the R$^3$ ring, with the proviso that R$^3$ is not a pyridine ring, with X$^-$ as a counterion selected from the group consisting of Cl$^-$, OH$^-$, SO$_4$H$^-$, CH$_3$COO$^-$, and CF$_3$COO$^-$, BF$_4^-$, PF$_6^-$, SbF$_6^-$, CH$_3$SO$_3^-$, CF$_3$SO$_3^-$, and PhCO$_2^-$—;

(b) substituted, positively charged heteroaromatic rings linked to the triazine backbone through a nitrogen atom in the R$^3$ ring, wherein the substituents for R$^3$ are selected from the group consisting of alkyl, carboxyl, amino, alkoxy, thio, cyano, amide and ester groups, with X$^-$ as a counterion selected from the group consisting of Cl$^-$, OH$^-$, SO$_4$H$^-$, CH$_3$COO$^-$, and CF$_3$COO$^-$, BF$_4^-$, PF$_6^-$, SbF$_6^-$, CH$_3$SO$_3^-$, CF$_3$SO$_3^-$, and PhCO$_2^-$; and (c) unsubstituted, positively charged pyridine rings linked to the triazine backbone through the nitrogen atom in the R$^3$ ring, with X$^-$ as a counterion selected from the group consisting of SO$_4$H$^-$, CH$_3$COO$^-$, and CF$_3$COO$^-$, BF$_4^-$, PF$_6^-$, SbF$_6^-$, CH$_3$SO$_3^-$, CF$_3$SO$_3^-$, and PhCO$_2^-$.

3. A liquid crystal display comprising an optical retardation plate, wherein the retardation plate comprises a substrate with a layer thereon, the layer comprising the following composition:

-continued wherein
R¹, which may be the same or different, is a hydrophilic group selected from the group consisting of carboxylic, sulfonic, sulfonamide and phosphate groups;
R², which may be the same or different, is selected from the group consisting of alkyl groups and hydrogen;
R³ is selected from the group consisting of:
  (a) unsubstituted, positively charged heteroaromatic rings linked to the triazine backbone through a nitrogen atom in the R³ ring, with the proviso that R³ is not a pyridine ring, with X⁻ as a counterion selected from the group consisting of Cl⁻, OH⁻, SO₄H⁻, CH₃COO⁻, and CF₃COO⁻, BF₄⁻, PF₆⁻, SbF₆⁻, CH₃SO₃⁻, CF₃SO₃⁻, and PhCO₂⁻—;
  (b) substituted, positively charged heteroaromatic rings linked to the triazine backbone through a nitrogen atom in the R³ ring, wherein the substituents for R³ are selected from the group consisting of alkyl, carboxyl, amino, alkoxy, thio, cyano, amide and ester groups, with X⁻ as a counterion selected from the group consisting of Cl⁻, OH⁻, SO₄H⁻, CH₃COO⁻, and CF₃COO⁻, BF₄⁻, PF₆⁻, SbF₆⁻, CH₃SO₃⁻, CF₃SO₃⁻, and PhCO₂⁻; and
  (c) unsubstituted, positively charged pyridine rings linked to the triazine backbone through the nitrogen atom in the R³ ring, with X⁻ as a counterion selected from the group consisting of SO₄H⁻, CH₃COO⁻, and CF₃COO⁻, BF₄⁻, PF₆⁻, SbF₆⁻, CH₃SO₃⁻, CF₃SO₃⁻, and PhCO₂⁻.

4. An electronic device comprising a display, wherein the display comprises an optical retardation plate, and wherein the retardation plate comprises a substrate with a layer thereon, the layer comprising the following composition:

or wherein
R¹, which may be the same or different, is a hydrophilic group selected from the group consisting of carboxylic, sulfonic, sulfonamide and phosphate groups;
R², which may be the same or different, is selected from the group consisting of alkyl groups and hydrogen;
R³ is selected from the group consisting of:
  (a) unsubstituted, positively charged heteroaromatic rings linked to the triazine backbone through a nitrogen atom in the R³ ring, with the proviso that R³ is not a pyridine ring, with X⁻ as a counterion selected from the group consisting of Cl⁻, OH⁻, SO₄H⁻, CH₃COO⁻, and CF₃COO⁻, BF₄⁻, PF₆⁻, SbF₆⁻, CH₃SO₃⁻, CF₃SO₃⁻—, and PhCO₂⁻;
  (b) substituted, positively charged heteroaromatic rings linked to the triazine backbone through a nitrogen atom in the R³ ring, wherein the substituents for R³ are selected from the group consisting of alkyl, carboxyl, amino, alkoxy, thio, cyano, amide and ester groups, with X⁻ as a counterion selected from the group consisting of Cl⁻, OH⁻, SO₄H⁻, CH₃COO⁻, and CF₃COO⁻, BF₄⁻, PF₆⁻, SbF₆⁻, CH₃SO₃⁻, CF₃SO₃⁻, and PhCO₂⁻; and
  (c) unsubstituted, positively charged pyridine rings linked to the triazine backbone through the nitrogen atom in the R³ ring, with X⁻ as a counterion selected from the group consisting of SO₄H⁻, CH₃COO⁻, and CF₃COO⁻, BF₄⁻, PF₆⁻, SbF₆⁻, CH₃SO₃⁻, CF₃SO₃⁻, and PhCO₂⁻.

5. An optical retardation plate comprising a substrate with a layer thereon, the layer comprising the following composition:

or wherein
R¹, which may be the same or different, is selected from the group consisting of COOH and SO₃H;
R², which may be the same or different, is selected from the group consisting of H and CH₃;
R³ is a positively charged, substituted pyridine ring linked to the triazine backbone through a nitrogen atom in the pyridine ring, wherein the substituents for R³ are selected from the group consisting of alkyl, carboxyl, amino, alkoxy, thio, cyano, amide and ester groups; and
X⁻ is a counterion selected from the group consisting of HSO₄⁻, Cl⁻, CH₃COO⁻, and CF₃COO⁻.

6. An optical retardation plate as claimed in claim 1, wherein the substrate is selected from glass and a polymeric film.

7. An optical retardation plate as claimed in claim 6, wherein the polymeric film is birefringent.

8. An optical retardation plate as claimed in claim 6, wherein the polymeric film is selected from the group consisting of polyimide, polymethyl methacrylate, polyethylene terephthalate, polyamide, polyimide, polycarbonate, polystyrene, styrene-acrylonitrile and acrylonitrile-methylacrylate.

9. An optical retardation plate as claimed in claim 7, wherein the birefringent polymeric film is selected from the group consisting of tricellulose acetate, polystyrene, polypropylene, polyethylene terepthalate, styrene-acrylonitrile, methacrylonitrile, and styrene methacrylonitrile.

10. A display as claimed in claim 2, further comprising a light source and at least one polarizer.

11. A display as claimed in claim 3, further comprising a light source and at least one polarizer.

12. An electronic device as claimed in claim 4, wherein the display further comprises a light source and at least one polarizer.

13. An optical retardation plate as claimed in claim 5, wherein the substrate is selected from glass and a polymeric film.

14. An optical retardation plate as claimed in claim 13, wherein the polymeric film is birefringent.

15. An optical retardation plate as claimed in claim 13, wherein the polymeric film is selected from the group consisting of polyimide, polymethyl methacrylate, polyethylene terephthalate, polyamide, polyimide, polycarbonate, polystyrene, styrene-acrylonitrile and acrylonitrile-methylacrylate.

16. An optical retardation plate as claimed in claim 14, wherein the birefringent polymeric film is selected from the group consisting of tricellulose acetate, polystyrene, polypropylene, polyethylene terepthalate, styrene-acrylonitrile, methacrylonitrile, and styrene methacrylonitrile.

* * * * *